(12) United States Patent
Liu

(10) Patent No.: US 11,278,399 B2
(45) Date of Patent: Mar. 22, 2022

(54) HEART VALVE PROSTHESIS DEVICE AND LEAFLET AND STENT BODY THEREOF

(71) Applicant: LIFETECH SCIENTIFIC (SHENZHEN) CO., LTD, Shenzhen (CN)

(72) Inventor: Xiangdong Liu, Shenzhen (CN)

(73) Assignee: LIFETECH SCIENTIFIC (SHENZHEN) CO., LTD, Shenzhen (CN)

(*) Notice: Subject to any disclaimer, the term of this patent is extended or adjusted under 35 U.S.C. 154(b) by 447 days.

(21) Appl. No.: 16/470,382

(22) PCT Filed: Dec. 19, 2017

(86) PCT No.: PCT/CN2017/117127
§ 371 (c)(1),
(2) Date: Jul. 12, 2019

(87) PCT Pub. No.: WO2018/121341
PCT Pub. Date: Jul. 5, 2018

(65) Prior Publication Data
US 2020/0188095 A1  Jun. 18, 2020

(30) Foreign Application Priority Data
Dec. 30, 2016 (CN) .......................... 201611265946.6

(51) Int. Cl.
*A61F 2/24* (2006.01)

(52) U.S. Cl.
CPC .... *A61F 2/2418* (2013.01); *A61F 2230/0013* (2013.01)

(58) Field of Classification Search
CPC ........ A61F 2/24; A61F 2/2412; A61F 2/2415; A61F 2/2418
See application file for complete search history.

(56) References Cited

U.S. PATENT DOCUMENTS

2016/0317305 A1  11/2016  Pelled et al.

FOREIGN PATENT DOCUMENTS

| CN | 202223386 U | 5/2012 |
|----|-------------|--------|
| CN | 202568532 U | 12/2012 |
| CN | 103550015 A | 2/2014 |
| CN | 103781439 A | 5/2014 |

(Continued)

OTHER PUBLICATIONS

Indian Office Action dated Jun. 29, 2021, in connection with corresponding IN Application No. 201917028365 (5 pp.).

(Continued)

*Primary Examiner* — Jason-Dennis N Stewart
(74) *Attorney, Agent, or Firm* — Maier & Maier, PLLC

(57) ABSTRACT

A heart valve prosthesis device includes a tubular stent body having an inflow end and an outflow end; a leaflet disposed in the lumen of the stent body; and fixing structures connected with the stent body and configured to fix the leaflet on the stent body. The leaflet includes at least two halves, and a connecting portion(s) connecting two adjacent halves. The fixing structure includes a closed hollow portion located on the stent body, and a fixing rod disposed in the hollow portion; one end of the fixing rod is connected to the hollow portion, and the other end is a free end; the connecting portion is hung on the fixing rod from the free end so as to fix the leaflet on the stent body.

20 Claims, 12 Drawing Sheets

(56) References Cited

FOREIGN PATENT DOCUMENTS

| CN | 105380730 A | 3/2016 |
| CN | 206934215 U | 1/2018 |
| JP | 2015-517376 A | 6/2015 |
| JP | 2016-107078 A | 6/2016 |

OTHER PUBLICATIONS

International Search Report dated Mar. 27, 2018 in corresponding International application No. PCT/CN2017/117127; pages.

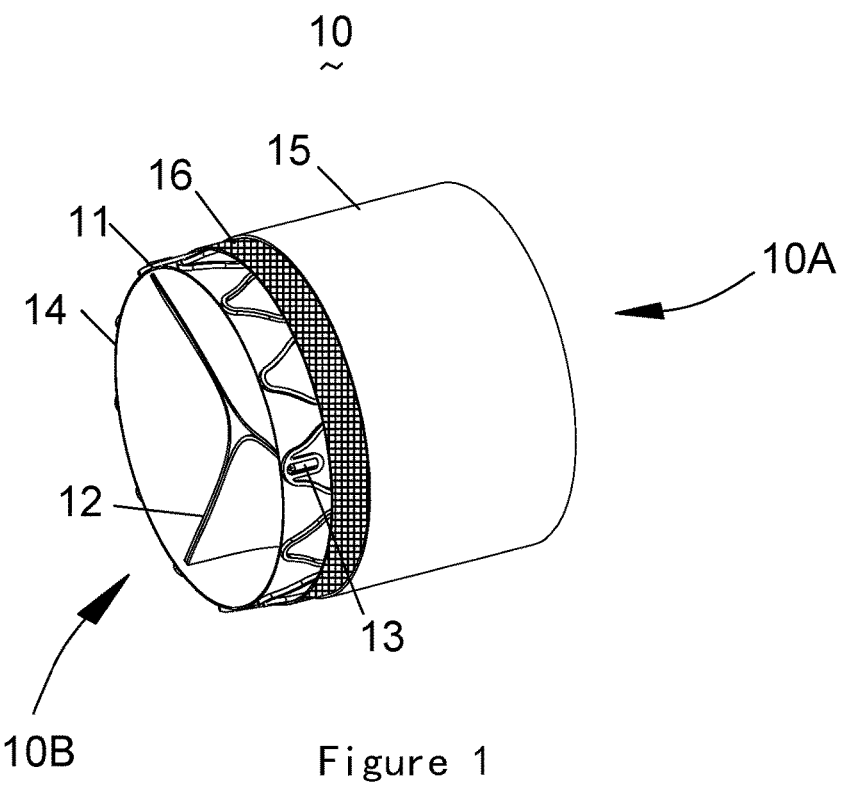
Figure 1
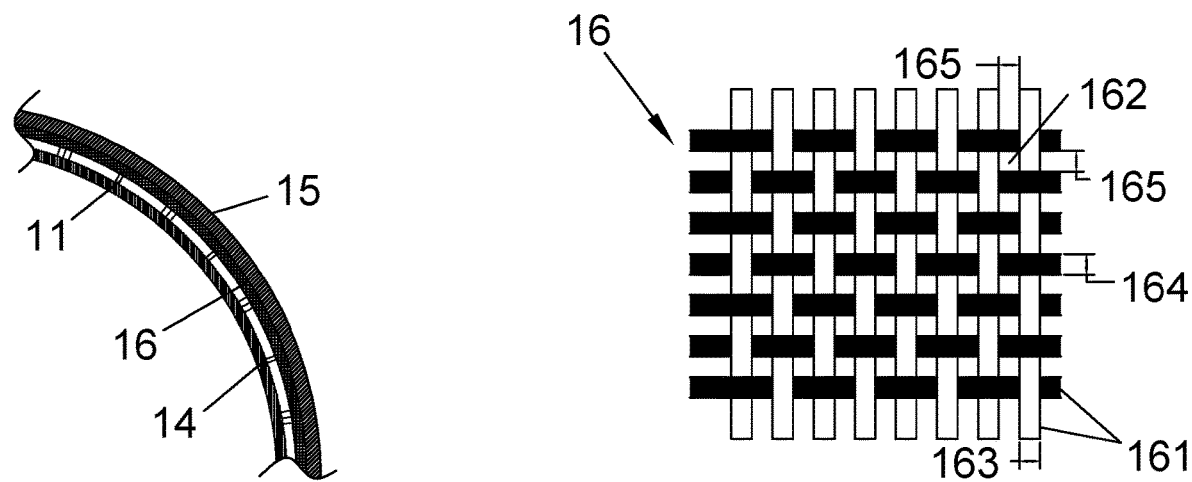
Figure 2a                    Figure 2b

HEART VALVE PROSTHESIS DEVICE AND LEAFLET AND STENT BODY THEREOF

FIELD

The present application relates to cardiovascular medical devices, and more particularly relates to an artificial heart valve device for replacing a natural heart valve, and a leaflet and a stent body thereof.

BACKGROUND

Main causes of valve diseases include rheumatic fever, mucinous degeneration, intervertebral disc degeneration, congenital malformation, ischemic necrosis, infection, trauma and the like, which may cause lesions of a single valve or multiple valves. Valvular lesions generally includes stenosis or insufficiency. The stenosis generally means that the opening of the valve is narrowed to decrease blood entering the next heart chamber. The insufficiency means that the valve does not close fully and there is backflow of part of the blood. The stenosis and/or the insufficiency would obstruct normal blood flow to increase the corresponding heart burden, thus causing impairment to normal functions of the heart and leading to cardiac failure and changes of functions of multiple visceral organs of organisms. There are two main surgical therapies for treating heart valve diseases at the present: 1) valvuloplasty, used for repairing a damaged valve, and 2) valve replacement, used for replacing the damaged valve with an artificial mechanical valve or a bioprosthetic valve. And there are two surgical pathways which are surgical operation and minimally invasive intervention.

The surgical operation is a common method for replacing or repairing a diseased or damaged valve. A defective heart valve is replaced by an artificial valve, and a low-calcified valve is repaired or rebuilt. However, high complications and high mortality rate are significant defects of the surgical operation. In recent years, percutaneous and minimally invasive valve implantation surgical methods have been developed. The percutaneous and minimally invasive surgical methods are used to implant valves into lesion locus through sheaths to reduce and avoid traumas and relevant complications of the surgical operation.

For example, the document No. CN105380730A discloses a minimally invasive implanted artificial valve device. As shown in FIGS. 26 to 29, a valve 10 is provided with a framework 12, a leaflet 14, an inner skirt 16 and an outer skirt 18. The leaflet 14 includes three lobules 40. Multiple fixing holes 20 spaced from one another are formed in the framework 12 in a circumferential direction. Upper protruding portions 112 of two lobules 40 are downwards folded, and lower protruding portions 116 of the two lobules 40 are inserted into the fixing holes 20 and extend out of the outer circumferential surface of the framework 12. The portion, extending out of the outer circumferential surface, of each lower protruding portion 116 is sutured to the corresponding upper protruding portion 112 with a main suture 150 to form a sutured portion 122 of a valve strut as shown in FIG. 24.

This valve device has the following defects: the sutured portion 122 of the valve strut is relatively thick, so that a relatively thick delivery sheath is needed to deliver the valve device, which increases the risk of damage to a blood vessel by the sheath in a surgical procedure and also leads to an inapplicability of the valve to a patient with relatively thin blood vessels.

SUMMARY

Exemplary embodiments of the present application provide an artificial heart valve device having a smaller size and longer service life, so as to overcome the defects in the prior art.

A solution adopted by the present application to solve the technical problem is may be as follows: an artificial heart valve device, including a tubular stent body having an inflow end, an outflow end and hollows, a leaflet arranged in a cavity of the stent body, and fixing structures connected with the stent body and configured for fixing the leaflet on the stent body, and the leaflet includes at least two valve lobules and a connecting portion connecting two adjacent valve lobules; where the fixing structure is arranged in the hollow, and includes a fixing rod and a main body connected with the stent body; the main body is provided with a through hole; at least a part of the fixing rod is located in the through hole; one end of the fixing rod is connected with the main body, and the other end of the fixing rod is a free end pointing to the outflow end; and the connecting portion passes through the through hole and is hung on the free end to fix the leaflet on the stent body.

Another exemplary solution adopted by the present application to solve the technical problem is as follows: an artificial heart valve device, includes a tubular stent body having an inflow end and an outflow end, a leaflet arranged in a cavity of the stent body, and fixing structures connected with the stent body and configured for fixing the leaflet on the stent body, and the leaflet includes at least two valve lobules and a connecting portion connecting two adjacent valve lobules; where the tubular stent body comprises closed frameworks; the framework includes a hollow; the fixing structure comprises a fixing rod located in the hollow; one end of the fixing rod is connected with the framework, and the other end of the fixing rod is a free end pointing to the outflow end; and the connecting portion bypasses the free end to fix the leaflet onto the stent body.

Another exemplary solution adopted by the present application to solve the technical problem is as follows: a stent body of an artificial heart valve device, having an inflow end, an outflow end and hollows and includes fixing structures for fixing a leaflet, where the fixing structure is arranged in the hollow, and includes a fixing rod and a main body connected with the stent body; the main body is provided with a through hole; at least a part of the fixing rod is located in the through hole; and one end of the fixing rod is connected with the main body, and the other end of the fixing rod is a free end pointing to the outflow end.

Embodiments of the fixing structures of the present application do not protrude from the pipe wall of the stent body. During assembling of the leaflet, only the connecting portions are hung on the fixing rods, so that the maximum outer diameter of the compressed valve is reduced, the size of a delivery sheath required by the valve is decreased, and the risk of damage to a blood vessel by the sheath in surgery is lowered. In addition, the requirement of the interventional valvular surgery for the size of a blood vessel of a patient is lowered, and the application scope of interventional valves is expanded.

BRIEF DESCRIPTION OF THE DRAWINGS

The present application will be further described below in combination with accompanying drawings and embodiments. In the drawings:

FIG. 1 is a structural schematic diagram of an artificial heart valve device provided by one embodiment of the present application;

FIG. 2a is a position relationship diagram of a middle layer of an artificial heart valve device as shown in FIG. 1 and inner and outer coating membranes;

FIG. 2b is a structural schematic diagram of a middle layer as shown in FIG. 2a;

FIG. 4 is a stereogram of a valve as shown in FIG. 3a;

DETAILED DESCRIPTION OF THE EMBODIMENTS

To understand the technical features, objectives and effects of the present application more clearly, specific implementation modes of the present application are described in detail now in contrast with accompanying drawings.

In a first exemplary embodiment, as shown in FIG. 1, an artificial heart valve device 10 includes a tubular stent body 11 having an inflow end 10A and an outflow end 10B, fixing structures 13 connected with the stent body 11 and a leaflet 12 arranged in a cavity of the tubular stent body 11. The stent body 11 is used for fixing the leaflet 12 and providing a radial tension to fix the artificial heart valve device 10 into a heart tissue at the same time. The leaflet 12 serves as a one-way valve and limits a one-way blood flow from the inflow end 10A to the outflow end 10B so as to achieve the effect of a human valve.

A stent body 11 may be made of a biocompatible plastic expansion material known in the art, such as medical stainless steel or a cobalt-chromium alloy, or made of a self-expandable material such as a nickel-titanium alloy. A stent body 11 made of a plastic expansion material may be compressed radially in a delivery sheath and is expanded to an initial shape and size through an inflatable balloon or an equivalent expansion mechanism. A stent body 11 made of a self-expandable material may be compressed radially in the delivery sheath and recovers the initial shape and size in the absence of the compression of the delivery sheath. A stent body 11 may be cut from a tube or woven from a metal wire.

Figure 5:
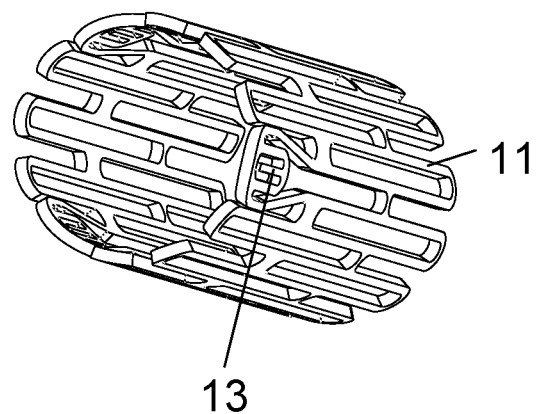
FIG. 5 is a structural schematic diagram of a stent body in a compressed state in an artificial heart valve device as shown in FIG. 1.
Figure 6:
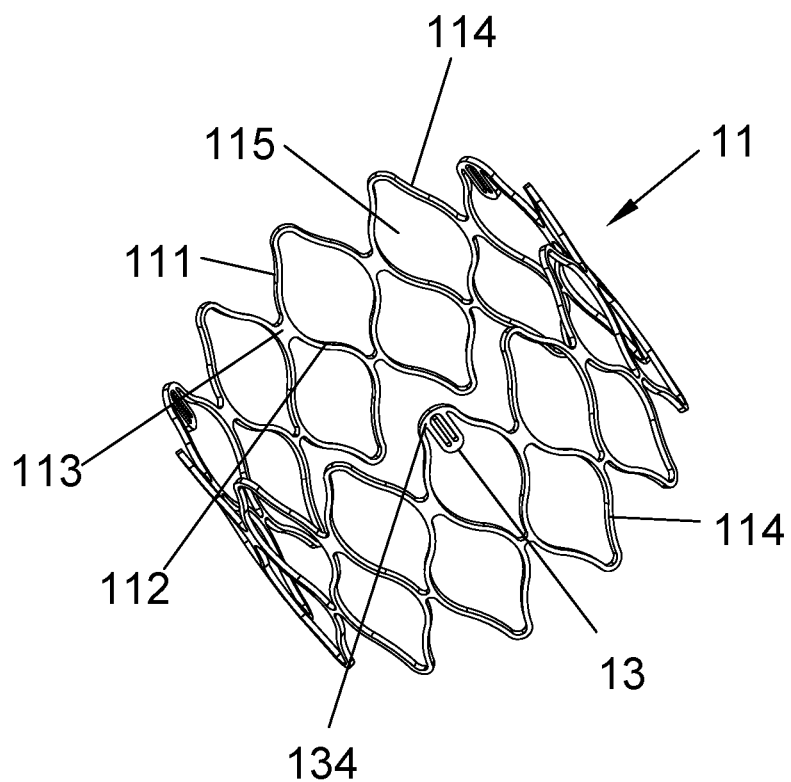
FIG. 6 is a structural schematic diagram of a stent body as shown in FIG. 5 in an expanded state.

A stent body 11 of the present embodiment is cut from a superelastic or shape memory nickel-titanium metal tube through laser while a tube has a diameter range of about 8-10 mm and a thickness range of about 0.3-0.5 mm, and the cut shape and structure are as shown in FIG. 5. As shown in FIG. 6, the stent body 11 includes multiple waveform ring-like portions 111 and 112 arranged along the axis of the stent body 11. The waveform phases of the waveform ring-like portions 111 and 112 are opposite, that is, the wave crests of the waveform ring-like portion 111 are opposite to the wave troughs of the waveform ring-like portion 112. The waveform ring-like portions 111 and 112 are connected through connecting points 113 so as to form multiple closed frameworks 114 arranged along a circumferential direction of the stent body 11. Each closed framework 114 is encircled by one wave crest of the waveform ring-like part 111 and one wave trough, opposite to the wave crest, of the waveform ring-like part 112 and has a hollow 115.

In addition, in the present embodiment, the inner and outer circumferential surfaces of a stent body 11 are covered by coating membranes. In other possible embodiments, only one of the inner and outer circumferential surfaces is covered by a coating membrane. Specifically, referring to FIGS. 1 to 2b and FIG. 6, the outer circumferential surface is covered by an outer coating membrane 15, and the inner circumferential surface is covered by an inner coating membrane 14. These inner and outer coating membranes are used for preventing streaming of blood flow at the hollows 115 of the stent body 11. An inner coating membrane 14 and an outer coating membrane 15 may be made of macromolecular materials with relatively high biocompatibility, such as ePTFE (e-polytetrafluoroethylene), PET (polyethylene glycol terephthalate) or PCU (polycarbonate polyurethane) and an animal pericardial tissue. A coating membrane may be in various forms, such as membranes, woven cloth, woven meshes, knitted fabrics, knitted nets and nonwoven cloth. An inner coating membrane 14 and an outer coating membrane 15 may be fixed onto a stent body 11 by a conventional process in the art, such as suturing, gluing and thermal covering, and may adopt different materials and forms or adopt the same materials and forms. For example, an inner coating membrane 14 is a PTFE woven mesh, and an outer coating membrane 15 is an ePTFE membrane. These two membranes are integrated at the hollows 115 of a stent body 11 through thermal covering, so as to fix the stent body 11 between them. Therefore, good suture performance may be achieved by use of the strength of the PTFE cloth, and leakage of the artificial heart valve device may be prevented by use of the good leakproof-ability (or ability to prevent leaks) of the ePTFE membrane.

To further improve the suture performance of a leaflet 12, the leakproof-ability (or ability to prevent leaks) of a stent body 11 and the bonding strength between coating membrane layers as well as the bonding strength between a coating membrane layer and a stent body 11, a middle layer 16 may be added between an inner coating membrane 14 and a stent body 11 or between an outer coating membrane 15 and a stent body 11. As shown in FIGS. 2a and 2b, in the present embodiment, a middle layer 16 is arranged between an outer coating membrane 15 and a stent body 11. A middle layer 16 may be single-layer or multilayer, and may be a woven mesh formed by PTFE wires, or a plain or oblique woven mesh tube arranged on the outer circumferential surface of a stent body 11 in a sleeving manner and formed by a PTFE wire. As shown in FIG. 2b, a middle layer 16 has a thickness range of about 0.06-0.72 mm and is woven from two strands of PTFE wires 161. A mesh 162 has an average width 165 range of about 0.05-0.4 mm, and the PTFE wire 161 has an average wire width range of about 0.05-0.6 mm.

An inner coating membrane 14 and an outer coating membrane 15 both adopt an ePTFE membranes having thickness range of about 0.1-0.4 mm, each of which is can have of 1 to 6 layers. A middle layer 16 is clamped between a stent body 11 and an outer coating membrane 15. The coating membranes, the middle layer and the stent body are fused together through a hot pressing method. At the hollows 115 of the stent body 11, the inner coating membrane 14, the middle layer 16 and the outer coating membrane 15 are fused together. The inner coating membrane 14 and the outer coating membrane 15 are fused together through the meshes 162 of the middle layer 16. To increase the bonding force of the coating membranes and the stent body 11, a PTFE coating layer or a Parylene coating layer may be deposited or sprayed on the surface of the stent body 11.

Figure 3A:
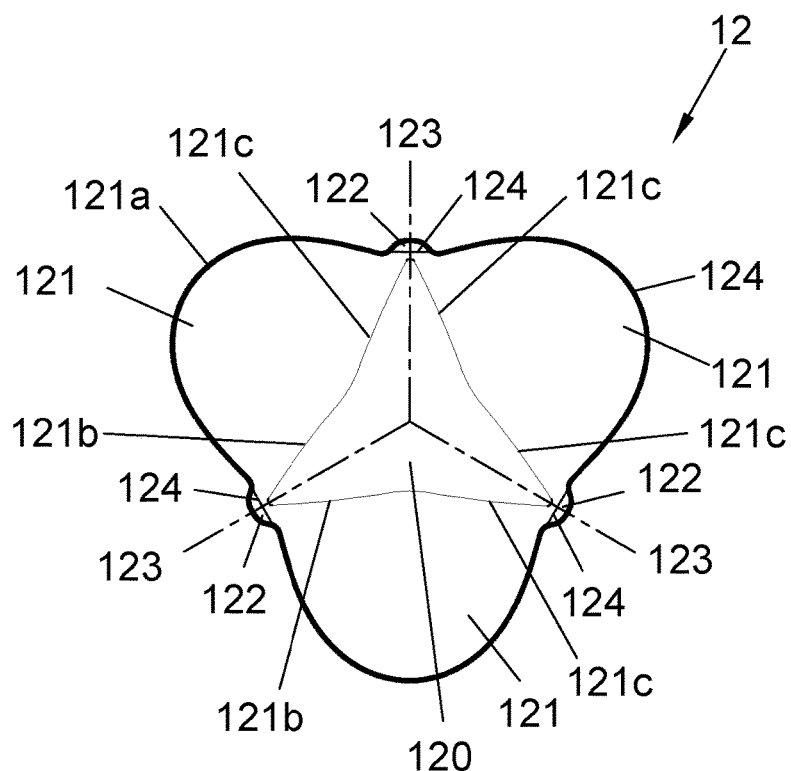
FIG. 3a is a planar expanded view of a valve in an artificial heart valve device as shown in FIG. 1.
Figure 3B:
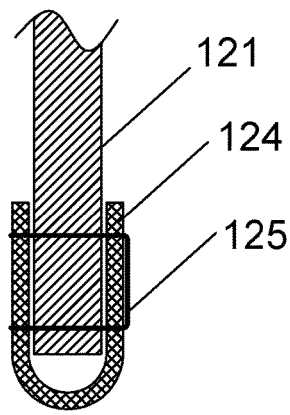
FIG. 3b is a partial schematic diagram of connection of a valve as shown in FIG. 3a and a reinforcing layer.
Figure 4:
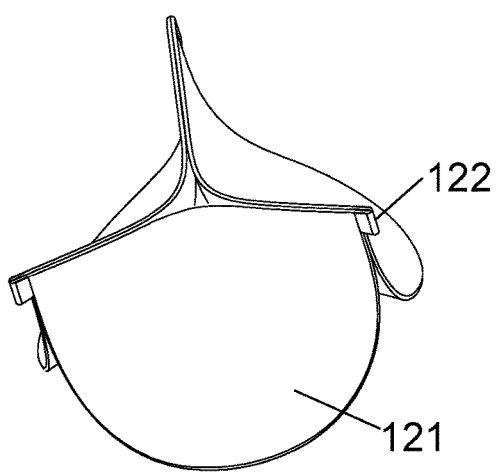

FIG. 3a and FIG. 4 are respectively a planar graph of a leaflet 12 expanded in a natural state and a stereo installation state diagram. In the present embodiment, a leaflet 12 is composed of three valve lobules 121 of same shapes and sizes and three connecting portions 122 of same shapes and sizes. Two adjacent valve lobules 121 are connected together through each connecting portion 122. The three valve lobules 121 respectively have bottom edges 121a, 121b and 121c, and are enclosed in the center of a leaflet 12 to form an approximately equilateral triangle-shaped center hole 120. The three valve lobules 121 form a leaflet body. Further, the three valve lobules 121 and the three connecting portions 122 are integrated, that is, each connecting portion 122 is part of the leaflet 12. As shown in FIGS. 3a and 3b, to improve the suture performance of the leaflet 12, a reinforcing layer 124 may be added at the edge of the leaflet 12. A reinforcing layer 124 covers the edge of the leaflet 12 and then is fixed through a suture 125. A reinforcing layer 124 may be made of ultrahigh molecular weight polyethylene, PET, nylon, PU, PCU and the like, and may be of different forms, such as a membrane and a woven fabric. A leaflet 12 is cut from an animal pericardium (such as a bovine pericardium or pig pericardium subjected to chemical curing treatment) or a macromolecular material (such as a PTFE membrane or cloth, an ultrahigh molecular weight polyethylene membrane or cloth, an aramid fiber membrane or cloth, a PCU membrane or cloth) through laser, a cutting die, a hydro jet or scissors and the like, and a cut form is as shown in FIG. 3a.

The outer contour line of the body of a leaflet is of an approximate regular triangle shape and has three smooth vertex angles. Each connecting portion 122 protrudes from the outer contour lines 124 of two valve lobules connected with the connecting portion. It is worth noting that each connecting portion 122 also may not exceed the outer contour lines 124. These three valve lobules 121 in a planar expanded state are arranged in a centrosymmetric manner along the circumferential direction of the stent body 11. The whole leaflet 12 is in mirrored symmetry along each symmetry line 123. The valve lobules 121 are downwards folded along the symmetry lines 123, and then the bottom edges 121b and 121c of two adjacent valve lobules 121 are aligned and fitted with each other to obtain an installation form of a leaflet 12 as shown in FIG. 4. An installed leaflet 12 has an effect similar to that of a one-way valve. The center hole 120 forms a blood flow channel, and the leaflet 12 allows the blood flow to flow from the inflow end 10A to the outflow end 10B, but does not allow the blood flow to flow from the outflow end 10B to the inflow end 10A. This is because when the blood flow flows from the outflow end 10B to the inflow end 10A, the three valve lobules 121 may get close towards the center under the action of blood pressure to close the center hole 120. On the contrary, the blood flow would flush to disperse the three valve lobules 121 towards a direction away from the center when flowing from the inflow end 10A to the outflow end 10B to open the center hole 120.

The connecting portions 122 are symmetric along the symmetry lines 123, and the end close to the outflow end 10B of each connecting portion 122 is closed, and the end close to the inflow end 10A of the connecting portion 122 is open. The folded connecting portions 122 are fixedly connected with the fixing structures 13 of the stent body 11. Referring to FIG. 1 and FIG. 4 together, except the bottom edges 121b and 121c, the edges of other parts of the valve lobules 121 are fixed at the inflow end 10A of the coated stent body 11 through sutures.

Figure 7:
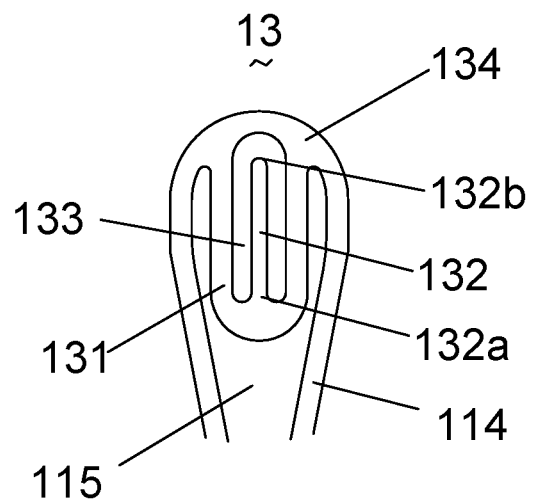
FIG. 7 is a structural schematic diagram of a first embodiment of a fixing structure in a stent body as shown in FIG. 5.

As shown in FIG. 6 and FIG. 7, in the present embodiment, a stent body 11 has wave crests 134. A fixing structure 13 includes a main body 131 and a fixing rod 132. A main body 131 is of an approximate U shape with two ends directly connected with a wave crest 134 and is provided with a through hole 133. A fixing rod 132 is arranged in each through hole 133. One end of a fixing rod 132 is connected with a main body 131, and the other end of a fixing rod 132 is a free end pointing to the outflow end.

A fixing structure 13 is located in a hollow 115, and is connected with the wave crest part of a waveform ring-like portion 111 close to the outflow end 10B and does not protrude from the inner wall and the outer wall of a stent body 11. The maximum width of a fixing structure 13 in a radial direction of a stent body 11 is less than or equal to the wall thickness of the stent body. That is to say, the positive projection of a fixing structure 13 in a plane perpendicular to the axial direction of the stent body 11 is located in the positive projection of the outer contour of the stent body 11 on the same plane. In other embodiments, a fixing structure 13 also may be connected with the wave trough part of a waveform ring-like portion 112. A fixing rod 132 has a fixed end 132a connected with a main body 131 and a free end 132b extending from the fixed end 132a towards the outflow end 10B, and a gap is reserved between the free end 132b and the wave crest 134. It can be understood that a free end 132b also may be in contact with a wave crest 134. A fixing rod 132 is located at the middle position in a main body 131, and the axis of a fixing rod 132 is approximately parallel to that of the stent body 11. Referring to FIG. 6 and FIG. 7 together, the open end of a connecting portion 122 may pass through a through hole 133 and bypass the free end 132b of a fixing rod 132, and the closed end of the connecting portion 122 is flush with the free end 132b to connect the connecting portion 122 to the fixing rod 132 in a sleeving manner. In other embodiments, a connecting portion 122 also may be of a barrel-shaped structure with one open end and one closed end. In addition, to further fix a connecting portion 122, enhance the connection between a connecting portion 122 and a fixing rod 132 and prevent the connecting portion 122 from falling off from the fixing rod 132, the connecting portion 122 may be fixed on the outer surface of the fixing rod 132 in a glue dispensing manner and the like. In the present embodiment, to further fix a connecting portion, two end portions of the folded connecting portion 122 are sutured with sutures. A U-shaped through hole 133 has a groove width ranging between about 0.2 and 0.4 mm which approximates to the thickness of the leaflet 12, and achieves an effect of fixing a connecting portion 122. A fixing rod 132 having a width ranging between about 0.1 and 0.4 mm does not protrude from the pipe wall of the stent body 11 and is used for hanging a connecting portion 122. The length of a fixing rod 132 is approximately equal to the maximum length of a connecting portion 122 on the symmetry axis of the corresponding leaflet body. Under reverse blood flow pressure, a leaflet 12 provides a radial tension for each of connecting portions 122 to prevent a prolapse of a valve lobule 121.

Figure 25:
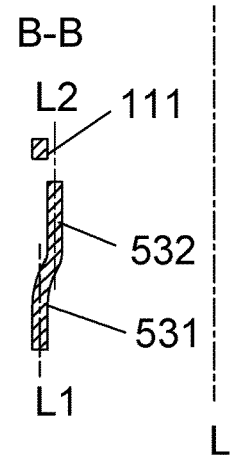
FIG. 25 is a cross sectional view of the fixing structure as shown in FIG. 24 along the direction B-B.
Figure 26:
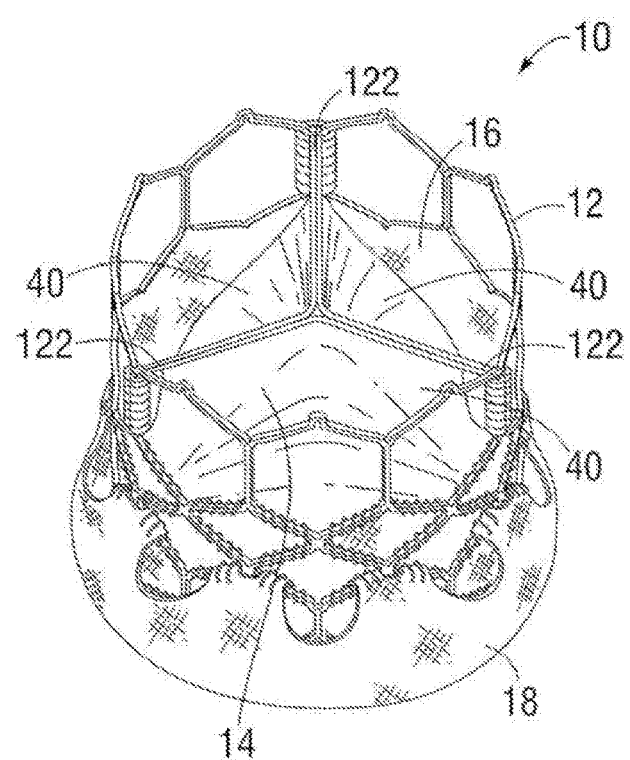
FIG. 26 is a structural schematic diagram of an artificial heart valve in the prior art.
Figure 27:
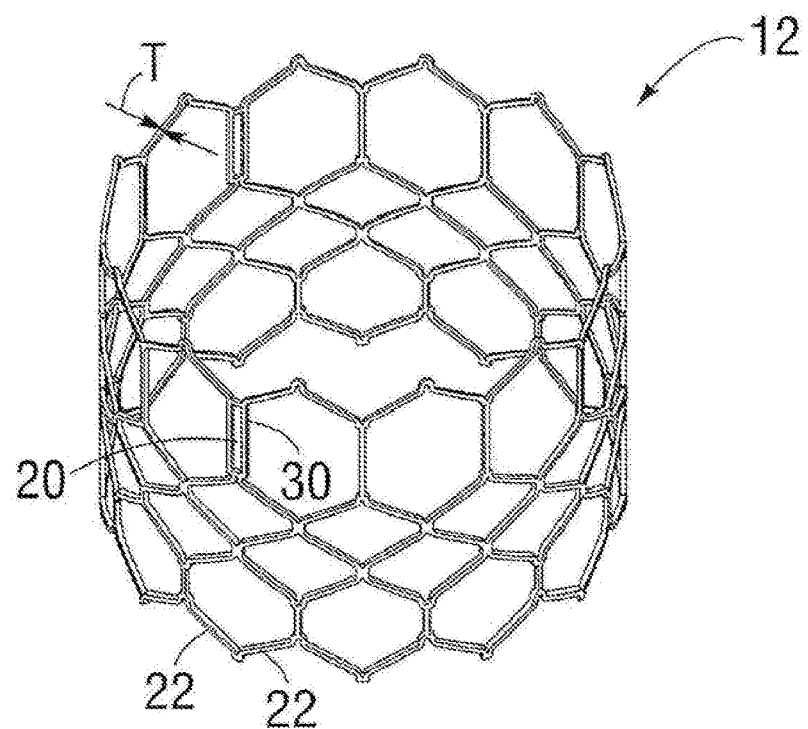
FIG. 27 is a structural schematic diagram of a framework in an artificial heart valve as shown in FIG. 26.
Figure 28:
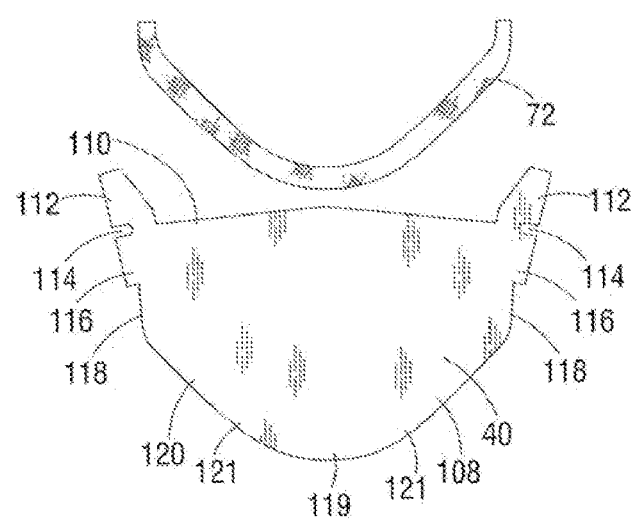
FIG. 28 is a structural schematic diagram of a lobule in an artificial heart valve as shown in FIG. 26.
Figure 29:
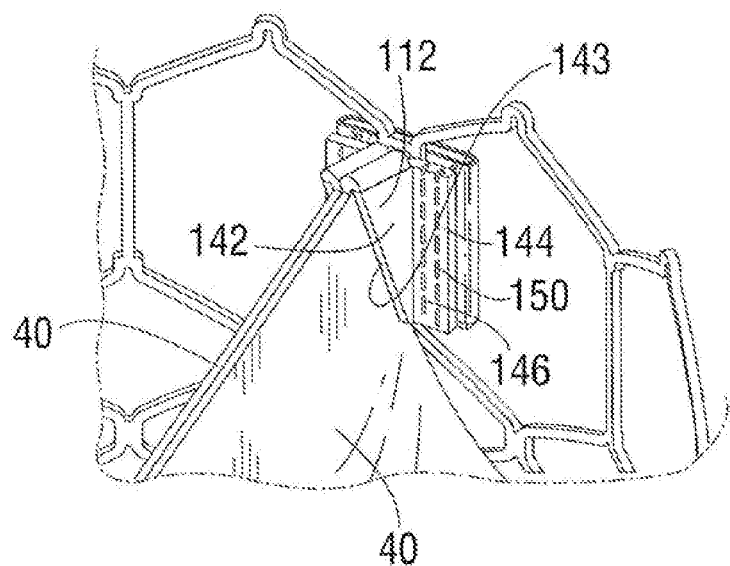
FIG. 29 is an assembling schematic diagram of a valve structure and the framework in an artificial heart valve as shown in FIG. 26.

On one hand, a fixing structures 13 of the present application are directly formed in a hollows 115 of the stent body, and a connecting portions 122 protrude from the contour line of the body of a leaflet 12 and may be folded to form a structure with one open end and one closed end; and after being folded along the center axis of the body of the leaflet, the connecting portions 122 may be directly hung on the fixing rods 132 to fix the leaflet 12 into the cavity of the stent body 11 and form a valve strut at the fixing rods 132. Compared with the prior art as shown in FIGS. 25 to 27, an artificial heart valve provided by the present application has the advantages that a leaflet 12 neither needs to extend out of the outer circumferential surface of a stent body 11 from fixing holes 20 to be folded nor needs to cover the stent body near a fixing holes 20 to be sutured at the valve strut, that is, the thickness of an artificial heart valve provided by the present application at a valve strut is approximately equal to the sum of the thicknesses of a connecting portions 122 and the thicknesses of a fixing rods 132, so that an artificial heart valve may be used cooperatively with a relatively thin delivery sheath, and the risk of damage to a blood vessel by a sheath in a surgical procedure is lowered. In addition, the requirement of the interventional valvular surgery for the size of a blood vessel of a patient is lowered, and the application scope of interventional valves is expanded.

On the other hand, a leaflet of the present application does not have sutures for connecting valve lobules. The assembling is very simple as only folded connecting portions are enabled to pass through through holes 133 and are arranged into fixing rods in a sleeved manner from the free ends of fixing rods. Furthermore, as the main body and the wave crest part of the waveform ring-like portion form a closed accommodating space to limit the movement of the leaflet in the axial direction and the axial prolapse of the leaflet is avoided, the connecting portions are not required to be sutured and fixed after being arranged into the fixing rods in the sleeved manner. Since the connecting portions are not required to be sutured and fixed, no pin holes would be produced, so that the mechanical strength and the fatigue life of the leaflet are improved. In addition, the connecting portions may be fixed through the through holes of the main bodies, the fixing rods and the wave crest parts without introducing other fixing structures, so that unnecessary affiliated fixing structures are reduced, and the maximum outer diameter of the compressed valve is decreased to the maximum extent, and adverse effects on a human body caused by the protruding affiliated fixing structures are also avoided.

Figure 10:
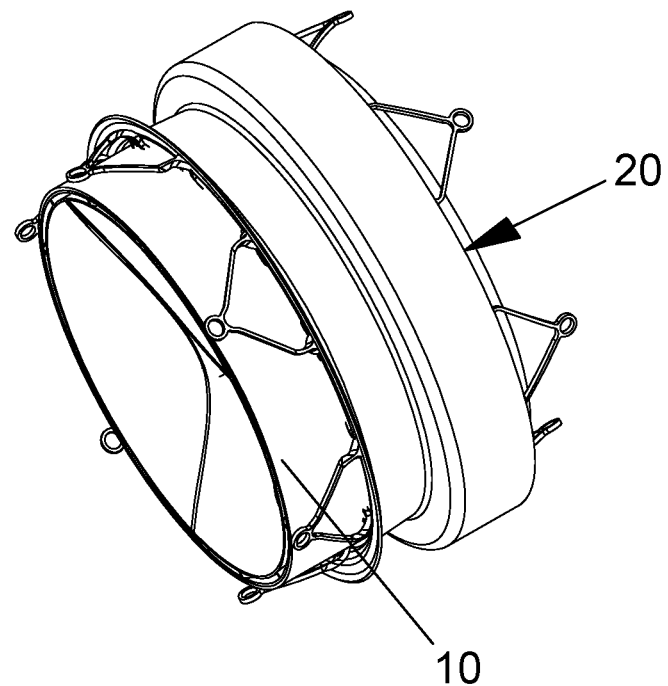
FIG. 10 is an assembled drawing of an artificial heart valve device as shown in FIG. 1 and a skirt structure.
Figure 11:
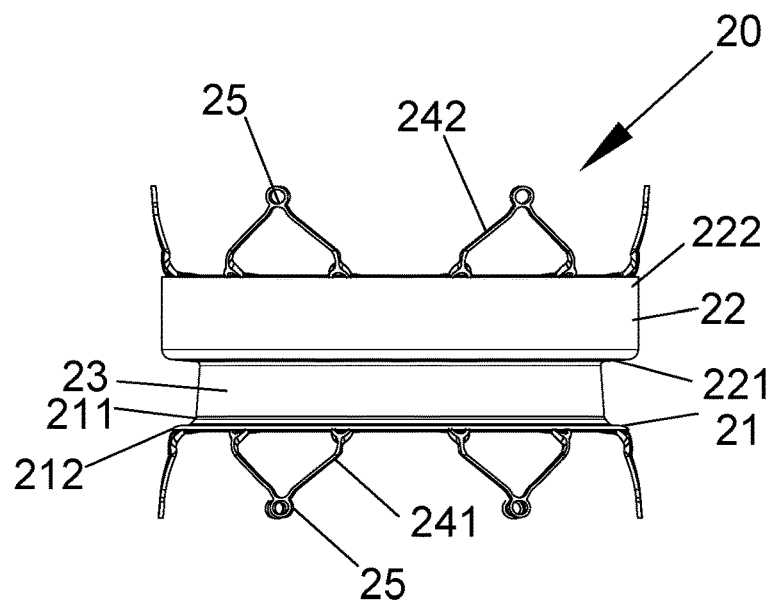
FIG. 11 is a front view of a skirt structure as shown in FIG. 10.
Figure 12:
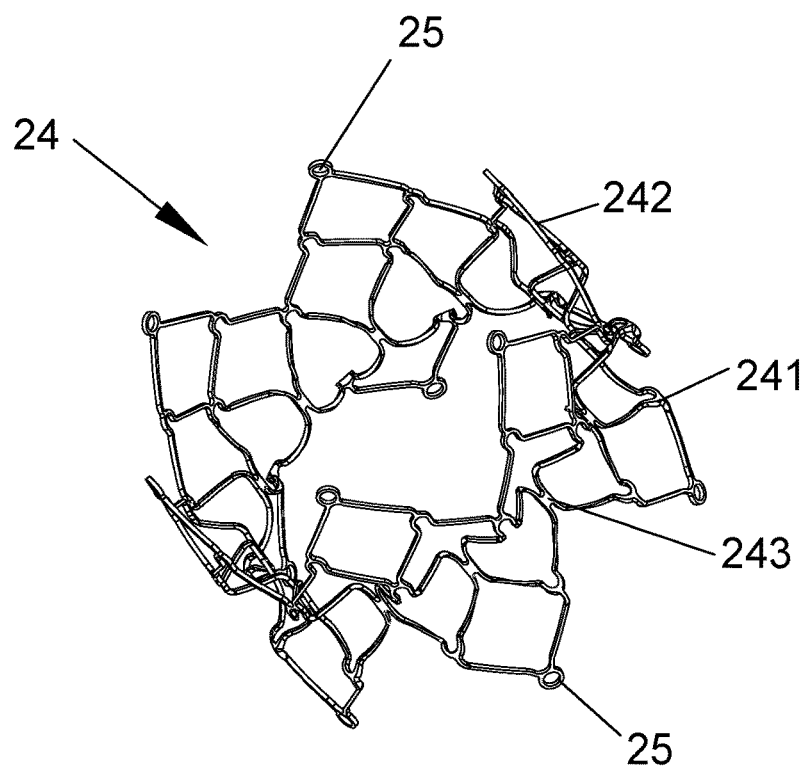
FIG. 12 is a structural schematic diagram of a skirt stent in a skirt structure as shown in FIG. 10.

As shown in FIG. 10, an artificial heart valve device 10 may further include a skirt structure 20 connected with the stent body 11. When an artificial heart valve device 10 is applied to a mitral valve or a tricuspid valve, a skirt structure 20 is needed on the basis of the artificial heart valve device 10 to prevent occurrence of perivalvular leakage. As shown in FIG. 11 and FIG. 12, the skirt structure 20 includes an atrium side skirt 22 and a ventricle side skirt 21, or only includes one side skirt. The atrium side skirt 22 and the ventricle side skirt 21 are connected through a waist portion 23.

An atrium side skirt 22 includes an atrium side skirt stent 242 and a flow resisting body covering the atrium side skirt stent, and has a closed end 221 and a free end 222 extending from the closed end 221 towards the inflow end 10A. Similarly, a ventricle side skirt 21 also includes a ventricle side skirt stent 241 and a flow resisting body covering the ventricle side skirt stent, and has a closed end 211 and a free end 212 extending from the closed end 211 towards the outflow end 10B. The extension of the free end towards the inflow end 10A is to avoid a cutting effect between it and a peripheral tissue of the atrium. The closed end 221 of an atrium side skirt stent 242 is connected with the closed end 211 of a ventricle side skirt stent 241 through a waist portion stent 243 welded on the stent body 11. By the arrangement of the flow resisting bodies on the atrium side skirt stent 242, the ventricle side skirt stent 241 and the waist portion stent 243, a better perivalvular leakage avoided effect may be achieved. Each flow resisting body may be various materials, such as an animal pericardium, PTFE, high molecular weight polyethylene, PET, nylon, PU and PCU, and also may be of various forms, such as a membrane, a woven fabric, a knitted fabric and nonwoven cloth. The flow resisting bodies may be fixed on the stent in various ways, for example by suturing, thermal covering, gluing and the like.

In addition, to facilitate connection of an artificial heart valve device having a skirt to a delivery system, at least one of the ventricle side skirt stent 241 and the atrium side skirt stent 242 is provided with connecting structures 25. In the present embodiment, connecting structures 25 are connecting rings arranged along the circumferential directions of the respective free ends of the atrium side skirt stent 242 and the ventricle side skirt stent 241 in a spaced apart manner.

Figure 8:
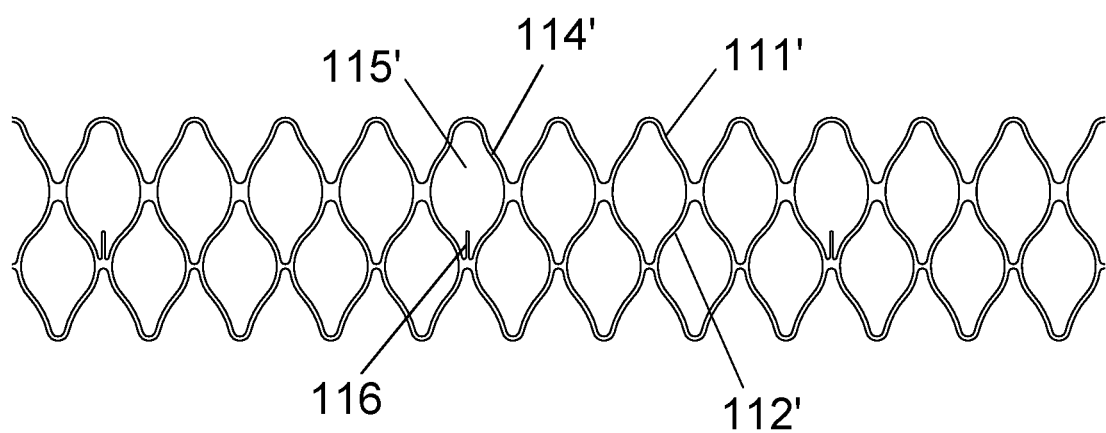
FIG. 8 is a structural schematic diagram of one embodiment of a fixing structure provided by one embodiment of the present application.

As shown in FIG. 8, in another embodiment of the present application, a stent body includes multiple closed frameworks 114' encircled by two adjacent waveform ring-like objects 111' and 112' having opposite phases and hollows 115'. The fixing rods 116 are located in the hollows 133'. One end of each fixing rod is connected with the wave trough of each framework 114', and the free end of the fixing rod points to the outflow end.

Figure 9:
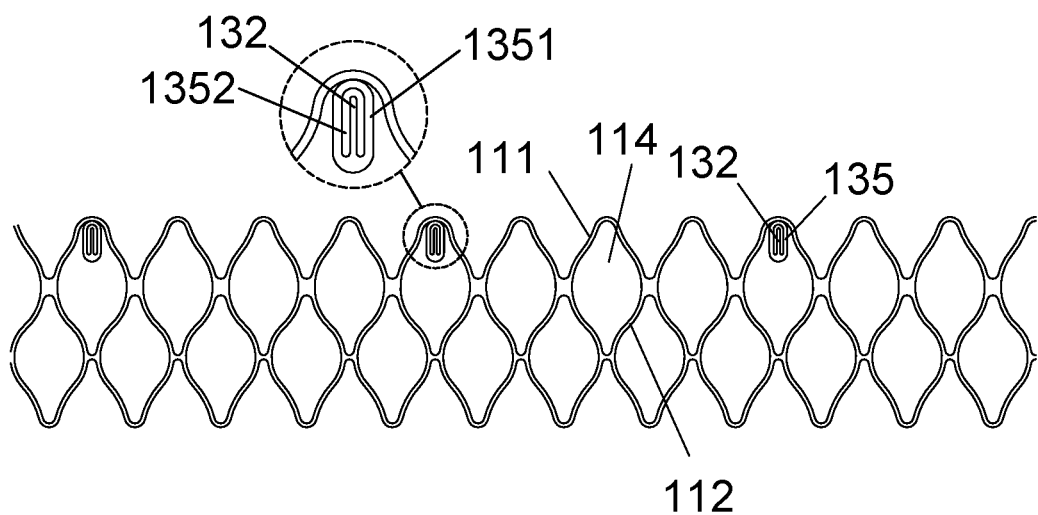
FIG. 9 is a structural schematic diagram of another embodiment of a fixing structure provided by one embodiment of the present application.

As shown in FIG. 9, in another embodiment of the present application, a stent body includes multiple closed frameworks encircled by two adjacent waveform ring-like objects having opposite phases and has hollows 114. Each fixing structure 135 is arranged in a hollow 114 and includes a closed annular main body 1351 and a fixing rod 132. Each main body 1351 is provided with an approximately U-shaped through hole 1352. One end of each fixing rod 132 is connected with each main body 1351, and the other end of the fixing rod 132 is a free end pointing to the outflow end. The end, not connected with the fixing rod 132, of each main body 1351 is connected with one wave crest of the stent body.

It can be understood that in other embodiments of the present application, each fixing structure 135 is still located in a hollow 114, but is connected with one wave trough of the stent body 1353 as long as the free end of each fixing rod 132 points to the outflow end.

Figure 13:
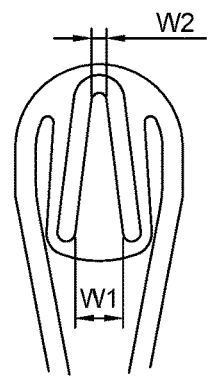
FIG. 13 is a structural schematic diagram of a second embodiment of a fixing structure in the artificial heart valve device provided by the present application.

FIG. 13 is a structural schematic diagram of a second embodiment of a fixing structure in a artificial heart valve device of the present application. In the present embodiment, a fixing structure is located in the closed framework of a stent body as shown in FIG. 6 and also includes a main body connected with one wave crest of a stent body and provided with a through hole, and a fixing rod located in the through hole and extending from the main body towards the outflow end. The fixing structure of the present embodiment has the same effect as the fixing structure 13 as shown in FIG. 7, but a difference lies in that in the present embodiment, the fixing rod is approximately triangular, like a fan. Specifically, the width W1 of the fixed end of a fixing rod is greater than the width W2 of the free end. The fixing rod divides the fixing structure into an inverted V-shaped accommodating groove having an equal groove width to accommodate the connecting portion. The connecting portion 122 of the leaflet 12 is of a fan-shaped structure (as shown in FIG. 3a), so that the similarly fan-shaped fixing rod may be well matched with the connecting portion 122 to enable the connecting portion 122 to well cover the outer side of the stent body 11 without producing protrusions and further decrease the maximum diameter of the compressed valve.

Figure 14:
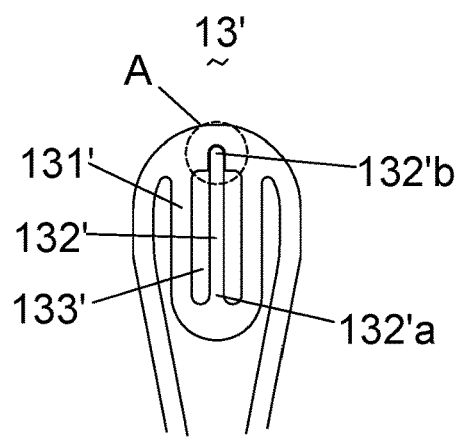
FIG. 14 is a structural schematic diagram of a third embodiment of a fixing structure in the artificial heart valve device provided by the present application.
Figure 15:
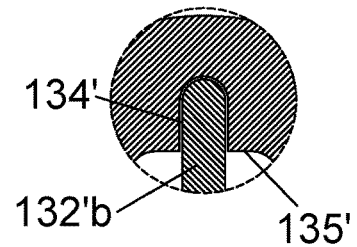
FIG. 15 is an enlarged view of the part A in FIG. 14.

FIG. 14 and FIG. 15 show structural schematic diagrams of a third embodiment of a fixing structure in an artificial heart valve device of the present application. In the present embodiment, the fixing structure 13' also includes a main body 131', a through hole 133' and a fixing rod 132' located in the through hole 133' and extending from the main body 131' towards the outflow end and has the same effect as the fixing structure 135 as shown in FIG. 9. But a difference lies in that the length of the fixing rod 132' is greater than that of an accommodating slot 133' along the axial direction of the stent body. In the present embodiment, the wave crest part of the stent body is further provided with an accommodating hole 134' communicated with the through hole 133'. The free end 132'*b* of a fixing rod 132' extends into the accommodating hole 134', and a gap is reserved between the free end 132' and the stent body 11 so as to move the free end 132' during subsequent fixing of the leaflet and to reset the free end 132' after the leaflet is fixed. The accommodating hole 134' is specifically formed in the wave crest part of the waveform ring-like portion 111, that is, the wave crest part is inwards sunken to form the above-mentioned accommodating hole 134'. The width of the gap between the free end 132*b*' and the wave crest part is equal to the size of a laser light spot and is about 0.01-0.03 mm. The free end 132'*b* of the fixing rod 132' may be turned out from the gap to hang the connecting portion 122 of the leaflet 12. In addition, due to the gap being much smaller than the thickness of the leaflet 12 and the effect of a stop portion 135' on the stent body 11, the connecting portion 122 of the leaflet 12 may be prevented from falling off from the fixing rod 132'.

Figure 16:
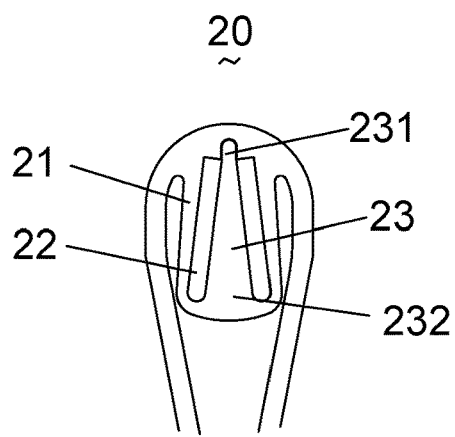
FIG. 16 is a structural schematic diagram of a fourth embodiment of a fixing structure in the artificial heart valve device provided by the present application.

FIG. 16 is a structural schematic diagram of a fourth embodiment of a fixing structure in an artificial heart valve device of the present application. A difference from the third embodiment lies in that in the present embodiment, the width of the fixed end 232 of a fixing rod 23 is greater than that of the free end 231 of the fixing rod 23 so as to better adapt to the similarly fan-shaped structure of the connecting portion 122.

Figure 17:
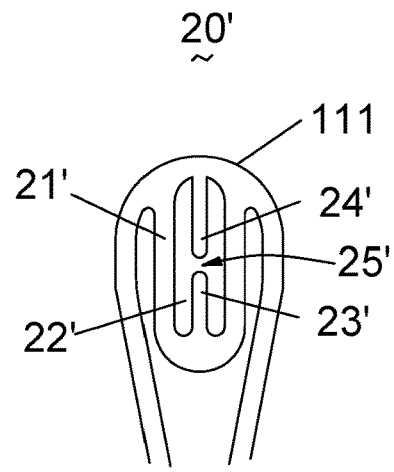
FIG. 17 is a structural schematic diagram of a fifth embodiment of a fixing structure in the artificial heart valve device provided by the present application.

As shown in FIG. 17, in the present embodiment, a fixing structure 20' includes a main body 21' connected with the stent body 11, a through hole 22' and a fixing rod located in the through hole 22'. In the present embodiment, the fixing rod includes a first fixing rod 23' and a second fixing rod 24'. The first fixing rod 23' extends from the main body 21' towards the outflow end 10B along the axis of the stent body 11. One end of the second fixing rod 24' is connected with one wave crest of the stent body 11, and the other end of the second fixing rod 24' is a free end and extends towards the inflow end 10A along the axis of the stent body 11. A gap 25' is reserved between the free ends of the first fixing rod 23' and the second fixing rod 24'. The connecting portion 122 of the leaflet 12 passes through the through hole 22' through the gap 25' and then is hung on the first fixing rod 23' and the second fixing rod 24'. When hung on the first fixing rod 23' and the second fixing rod 24', the connecting portion 122 of the leaflet 12 is well secured, making it very hard to fall off or otherwise be removed from the first fixing rod 23' and the second fixing rod 24' under any forces in any axial directions, so that the risk that the connecting portion 122 of the leaflet 12 falls off from the fixing rod is decreased.

Figure 18:
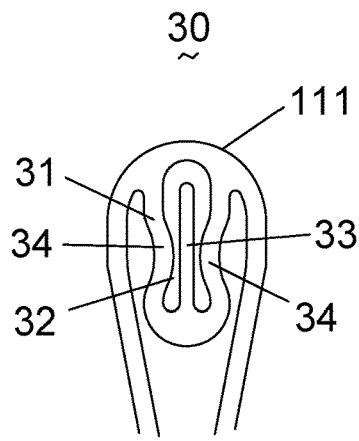
FIG. 18 is a structural schematic diagram of a sixth embodiment of a fixing structure in the artificial heart valve device provided by the present application.

As shown in FIG. 18, in the present embodiment, a fixing structure 30 also includes an approximately U-shaped main body 31 with two ends directly connected with one wave crest 111 of the stent body, and a fixing rod 33 located in a through hole 32 of the main body 31 and extending from the main body 31 towards the outflow end 10B. A difference from above-mentioned embodiments lies in that the surface, close to the through hole 32, of the main body 31 is further provided with protruding portions 34 protruding towards the fixing rod 33. The protruding portions 34 respectively located on two sides of the fixing rod 33 have arc-shaped outer surfaces which may not puncture the connecting portion 122 of the leaflet 12.

The protruding portions 34 narrow the through hole 32 on two sides of the fixing rod 33. The protruding portions 34 may expand outwards appropriately when clamping the connecting portion 122 of the leaflet 12 and provide an inwards counteractive clamping force for the connecting portion 122 of the leaflet 12 at the same time. This clamping force may reduce the slippage of a connecting portion 122 of a leaflet 12 in a through hole 32 and lower the risk that a connecting portion 122 falls off from a fixing rod 33.

Figure 19:
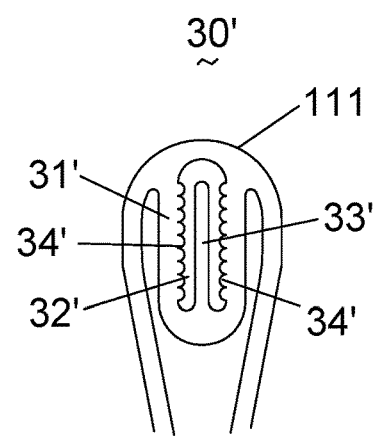
FIG. 19 is a structural schematic diagram of a seventh embodiment of a fixing structure in the artificial heart valve device provided by the present application.

As shown in FIG. 19, in the present embodiment, the structure of a fixing structure 30' is similar to that of the sixth embodiment. A difference lies in that in the present embodiment, the wavy outer surfaces of protruding portions 34' may disperse the clamping force of protruding portions 34' on a connecting portion 122 of a leaflet 12, so that excessive partial stress on the connecting portion 122 would be avoided when the connecting portion 122 is clamped.

Figure 20:
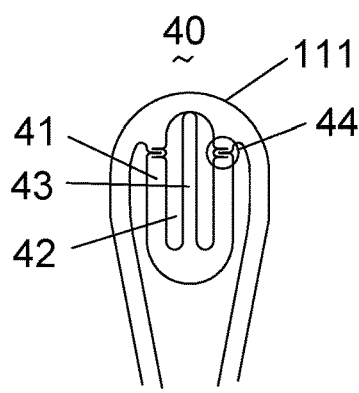
FIG. 20 is a structural schematic diagram of an elastic piece in an initial state in an eighth embodiment of a fixing structure in an artificial heart valve device provided by the present application.
Figure 21:
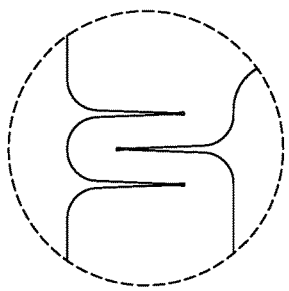
FIG. 21 is an enlarged view of part 44 in the fixing structure as shown in FIG. 20.

As shown in FIGS. 20 to 21, a fixing structure 40 also includes a main body 41 connected with one wave crest 111 of the stent body and a fixing rod 43 located in a through hole 42 of the main body 41 and extending from the main body 41 towards the outflow end 10B. A difference from above-mentioned embodiments lies in that two ends of the main body 41 are connected with the wave crest of the waveform ring-like portion 111 through elastic pieces 44. The elastic pieces 44 may extend under a tensile force and then can be restored to their initial shapes in the absence of a force. The elastic pieces 44 may be springs, or integrated Σ-shaped structures molded at two ends of the main body 41 through laser cutting as shown in the present embodiment.

Figure 22:
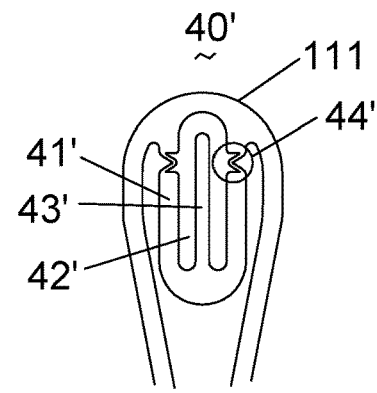
FIG. 22 is a structural schematic diagram of an elastic piece in a stretching state in the eighth embodiment of a fixing structure in an artificial heart valve device provided by the present application.
Figure 23:
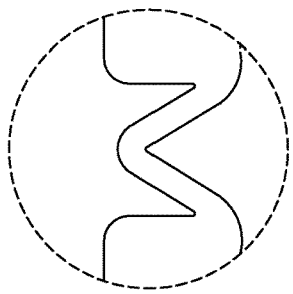
FIG. 23 is an enlarged view of part 44 in the fixing structure as shown in FIG. 22.

As shown in FIGS. 20 to 21, when the elastic pieces 44 are in the their initial shapes, the free end of the fixing rod 43 is in contact with the wave crest of the waveform ring-like portion 111 or the gap (less than the thickness of the leaflet 12) is extremely small. As shown in FIGS. 22 to 23, when the elastic pieces 44 are in the tensile states under a force, the gap between the free end of the fixing rod 43 and the wave crest of the waveform ring-like portion 111 is enlarged, and at the moment, the connecting portion 122 of the leaflet 12 may be hung on the fixing rod 43. Under an unstressed condition, the elastic pieces 44 restore the initial shapes as shown in FIG. 20, and at that moment, the free end of the fixing rod 43 is in contact with the wave crest part of the waveform ring-like portion 111 or the gap is extremely small, so that the risk that the connecting portion 122 of the leaflet 12 falls off from the fixing rod 43 may be lowered.

Figure 24:
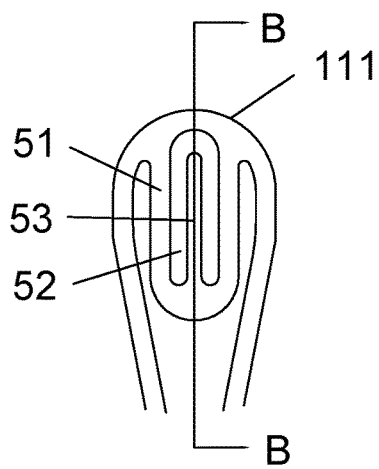
FIG. 24 is a structural schematic diagram of a ninth embodiment of a fixing structure in an artificial heart valve device provided by the present application.

As shown in FIG. 24 and FIG. 25, a fixing structure 50 also includes a main body 51 connected with one wave crest 111 of the stent body and a fixing rod 53 located in a through hole 52 of the main body 51 and extending from the main body 51 towards the outflow end 10B. A difference from above-mentioned embodiments lies in that the fixing rod 53 includes a first part 531 extending in the through hole 52 from the main body 51 along a direction parallel to the axis L of the stent body 11, and a second part 532 extending from the tail end of the first part 531 along a direction close to the axis L of the stent body 11. It can be seen from FIG. 23 that the axis L2 of the second part 532 is parallel to the axis L of the stent body 11, but is closer to the axis L of the stent body 11 than the axis L1. That is to say, the first part 531 is overlapped with the outer contour of the stent body 11, and the second part 532 protrudes from the inner wall of the stent body 11 and is located in a cavity of the stent body 11.

This "inwards sunken" structure of a fixing rod 53 allows a connecting portion 122 to be hung more easily. When the connecting portion 122 of a leaflet 12 is hung on a fixing rod 53, the protruding size of the outer side of the connecting portion 122 is decreased, which may reduce the difficulty of putting an artificial valve into a sheath and lower the risk of damage to the artificial valve in the processes of putting the artificial valve into the sheath and delivering the artificial valve.

Figure 30:
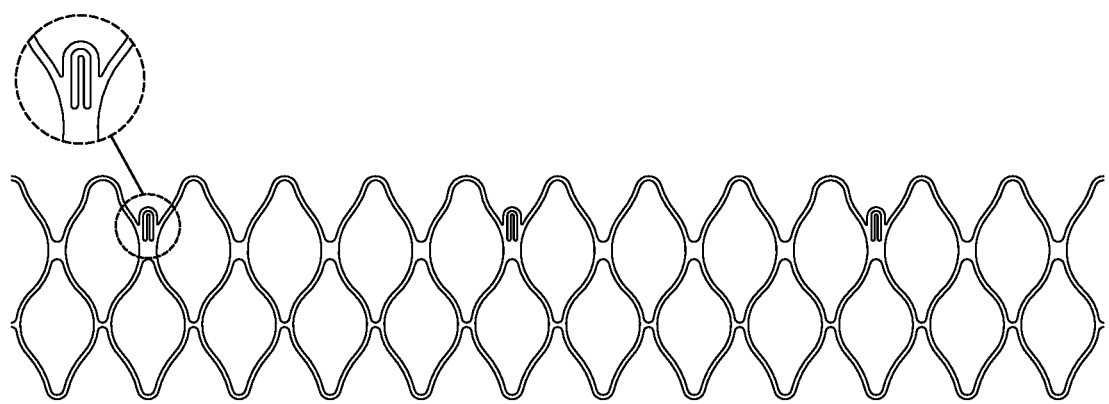
FIG. 30 is a structural schematic diagram of one type of fixing structures of the present application located at the open wave troughs of the stent body.

It can be understood that in other embodiments of the present application, a fixing structure having an approximately U-shaped main body as shown in FIGS. 5 to 7, FIG. 9 and FIGS. 13 to 25 may be located outside the closed framework structure. For example, as shown in FIG. 30, the fixing structure is located at the open wave trough of the stent body.

Figure 31:
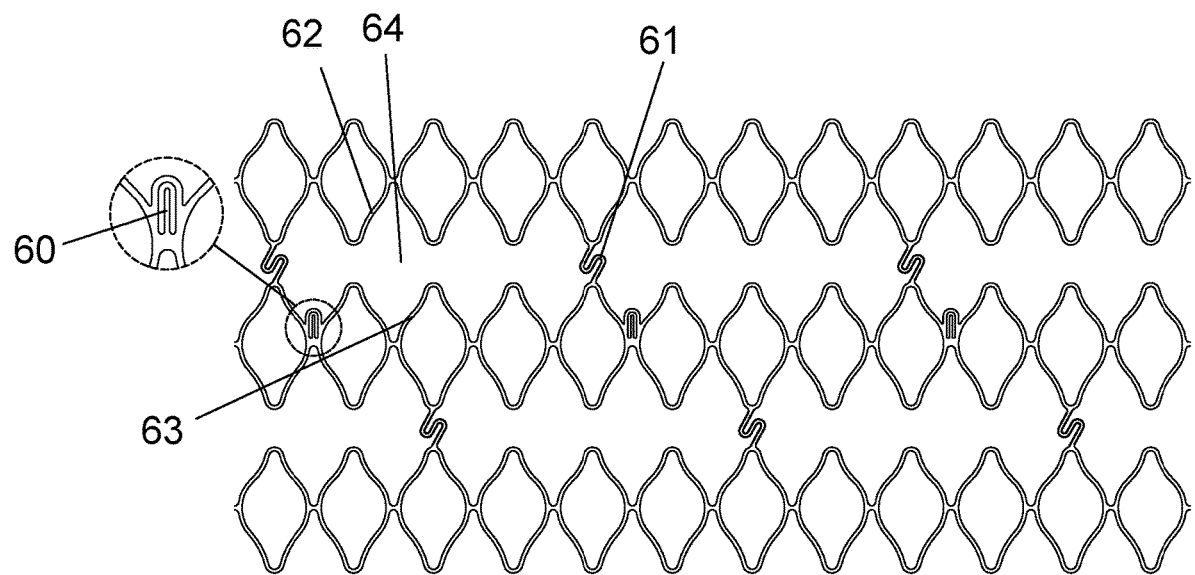
FIG. 31 is a structural schematic diagram of one type of fixing structures in the present application applied to another stent body.

In addition, as shown in FIG. 31, a stent body may further include multiple waveform ring-like portions 62 and 63 arranged along the axial direction of the stent body and spaced from one another, and connecting rods 61 located between two connected waveform ring-like portions 62 and 63 and connecting the two adjacent waveform ring-like portions 62 and 63. Each closed framework is encircled by the two adjacent waveform ring-like portions 62 and 63 and each connecting rod 61. One end of each fixing rod 60 is connected with the wave troughs of each waveform ring-like portion 63, and the other end of the fixing rod 60 points to the wave crests.

Figure 32:
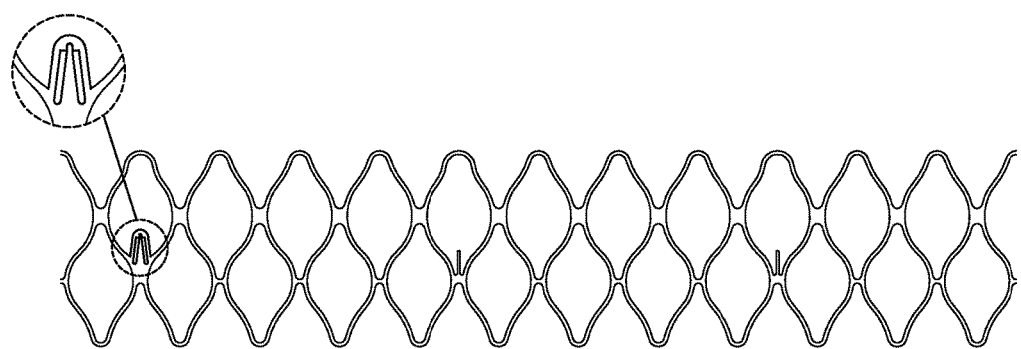
FIG. 32 is a structural schematic diagram of another type of fixing structures in the present application applied to the stent body of the present application.

Furthermore, as shown in FIG. 32, on the basis of the structure as shown in FIG. 8, the main body 131 of the structure as shown in FIG. 7 and FIGS. 13 to 23 also may be added, and a fixing rod 112 is changed into the structures as shown in FIG. 13 and FIGS. 16 to 25, thus obtaining the fixing structure located at the wave trough as shown in FIG. 8. However, a difference from FIG. 7 is that two ends of the main body are connected to the wave trough 132.

It can be understood that when the main body as shown in FIGS. 14 to 16 is added to the structure as shown in FIG. 8, the accommodating hole formed in the wave crest of the stent body as shown in FIGS. 14 to 16 may be formed in the end, not connected with the wave trough, of the main body, so as to accommodate the free end of the fixing rod 112.

The above embodiments merely express several implementation modes of the present application, and are described specifically and in detail, but are not limitations to the patent scope of the present application, therefore. It should be noted that those of ordinary skill in the art can make a variety of changes and improvements without departing from the idea of the present application, and these changes and improvements shall all fall within the protection scope of the present application.

The invention claimed is:

1. An artificial heart valve device, comprising:
 a tubular stent body having an inflow end, an outflow end and hollows, a leaflet arranged in a cavity of the stent body, and
 fixing structures connected with the stent body and configured for fixing the leaflet on the stent body, and the leaflet comprises at least two valve lobules and a connecting portion connecting two adjacent valve lobules;
 wherein the fixing structure is arranged in the hollows, and comprises a fixing rod and a main body connected with the stent body; the main body is provided with a through hole; at least a part of the fixing rod is located in the through hole; one end of the fixing rod is connected with the main body, and the other end of the fixing rod is a free end pointing to the outflow end; and the connecting portion passes through the through hole and is hung on the free end to fix the leaflet on the stent body.

2. The artificial heart valve device according to claim 1, wherein the main body is an approximate U shape with two ends of the U shape directly connected with the stent body.

3. The artificial heart valve device according to claim 1, wherein the main body is an approximate U shape with two ends of the U shape connected with the stent body through elastic pieces.

4. The artificial heart valve device according to claim 1, wherein the main body is a closed annular shape, and an end of the annular shape, not connected with the fixing rod, of the body is connected with the stent body.

5. The artificial heart valve device according to claim 1, wherein an accommodating hole communicated with the through hole is also formed in the stent body; the end portion of the free end is located in the accommodating hole; and a gap is reserved between the free end and the stent body.

6. The artificial heart valve device according to claim 1, wherein the fixing rod comprises a first fixing rod and a second fixing rod which are both located in the through hole; one end of the first fixing rod is connected with the main body, and the free end of the first fixing rod points to the outflow end; and one end of the second fixing rod is connected with the stent body, and the free end of the second fixing rod points to the inflow end.

7. The artificial heart valve device according to claim 1, wherein the fixing rod comprises a first part extending in the through hole from the main body along a direction parallel to the axis of the stent body, and a second part extending from the tail end of the first part along a direction close to the axis of the stent body.

8. The artificial heart valve device according to claim 1, wherein the width of the end, connected with the main body, of the fixing rod is greater than that of the free end.

9. An artificial heart valve device, comprising:
a tubular stent body having an inflow end and an outflow end, a leaflet arranged in a cavity of the stent body, and fixing structures connected with the stent body and configured for fixing the leaflet on the stent body, and the leaflet comprises at least two valve lobules and a connecting portion connecting two adjacent valve lobules;
wherein the tubular stent body comprises closed frameworks;
the framework comprises a hollow; the fixing structure comprises a fixing rod located in the hollow;
one end of the fixing rod is connected with the framework, and the other end of the fixing rod is a free end pointing to the outflow end; and
the connecting portion bypasses the free end to fix the leaflet onto the stent body.

10. The artificial heart valve device according to claim 9, wherein the stent body comprises a plurality of waveform ring-like portions arranged along an axial direction of the stent body; the closed framework is encircled by wave crests and wave troughs of two adjacent waveform ring-like portions; and one end of the fixing rod is connected with the wave troughs, and the free end of the fixing rod points to the wave crests.

11. The artificial heart valve device according to claim 10, wherein the stent body comprises a plurality of waveform ring-like portions arranged along an axial direction of the stent body and spaced from one another, and connecting rods located between two connected waveform ring-like portions and connecting the two adjacent waveform ring-like portions; the closed framework is encircled by the two adjacent waveform ring-like portions and the connecting rods; and one end of the fixing rod is connected with the wave trough, and the free end of the fixing rod points to the wave crest.

12. The artificial heart valve device according to claim 9, wherein the fixing structure further comprises a main body; the main body is provided with a through hole; at least a part of the fixing rod is located in the through hole; and the main body is connected with the framework.

13. A stent body of an artificial heart valve device, having an inflow end, an outflow end and hollows and comprising fixing structures for fixing a leaflet, wherein the fixing structure is arranged in the hollow, and comprises:
a fixing rod and a main body connected with the stent body;
the main body is provided with a through hole;
at least a part of the fixing rod is located in the through hole; and
one end of the fixing rod is connected with the main body, and the other end of the fixing rod is a free end pointing to the outflow end.

14. The stent body of the artificial heart valve device according to claim 13, wherein the main body is an approximate U shape with two ends of the U shape directly connected with the stent body.

15. The stent body of the artificial heart valve device according to claim 13, wherein the main body is an approximate U shape with two ends of the U shape connected with the stent body through elastic pieces.

16. The stent body of the artificial heart valve device according to claim 13, wherein the main body is a closed ring shape, and an end of the closed ring shape, not connected with the fixing rod, of the body is connected with the stent body.

17. The stent body of the artificial heart valve device according to claim 13, wherein an accommodating hole communicated with the through hole is formed in the stent body; and an end portion of the free end is located in the accommodating hole.

18. The stent body of the artificial heart valve device according to claim 13, wherein the fixing rod comprises a first fixing rod and a second fixing rod which are both located in the through hole; one end of the first fixing rod is connected with the main body, and the free end of the first fixing rod points to the outflow end; and one end of the second fixing rod is connected with the stent body, and the free end of the second fixing rod points to the inflow end.

19. The stent body of the artificial heart valve device according to claim 13, wherein the fixing rod comprises a first part extending in the through hole from the main body along a direction parallel to the axis of the stent body, and a second part extending from the tail end of the first part along a direction close to the axis of the stent body.

20. The stent body of the artificial heart valve device according to claim 13, wherein the width of an end, connected with the main body, of the fixing rod is greater than that of the free end.

* * * * *